US012640238B2

(12) United States Patent (10) Patent No.: US 12,640,238 B2

Suntivich et al. (45) Date of Patent: May 26, 2026

(54) METHODS AND SYSTEMS FOR TREATING A HETEROGENEOUS MIXTURE OF MATERIALS

(71) Applicant: SIXONE LABS LTD., Burnaby (CA)

(72) Inventors: Jin Suntivich, Vancouver (CA);
Christopher Wai, Vancouver (CA)

(73) Assignee: Sixone Labs Ltd., Burnaby (CA)

( * ) Notice: Subject to any disclaimer, the term of this patent is extended or adjusted under 35 U.S.C. 154(b) by 0 days.

(21) Appl. No.: 19/021,586

(22) Filed: Jan. 15, 2025

(65) Prior Publication Data

US 2025/0157592 A1 May 15, 2025

Related U.S. Application Data

(63) Continuation of application No. PCT/CA2024/050619, filed on May 7, 2024.

(60) Provisional application No. 63/464,724, filed on May 8, 2023.

(51) Int. Cl.
G16C 20/30 (2019.01)
G16C 20/70 (2019.01)

(52) U.S. Cl.
CPC ............ *G16C 20/30* (2019.02); *G16C 20/70* (2019.02)

(58) Field of Classification Search
CPC ................................. G16C 20/30; G16C 20/70
See application file for complete search history.

(56) References Cited

U.S. PATENT DOCUMENTS

| | | | |
|---|---|---|---|
| 6,744,500 | B2 | 6/2004 | Bradbury et al. |
| 7,292,958 | B2 | 11/2007 | Ceder et al. |
| 7,310,581 | B2 | 12/2007 | Mound |
| 7,449,655 | B2 | 11/2008 | Cowling et al. |
| 9,194,745 | B2 | 11/2015 | Ackley et al. |
| 10,361,003 | B2 | 7/2019 | Segal et al. |
| 10,625,304 | B2 | 4/2020 | Kumar et al. |
| 11,021,589 | B2 | 6/2021 | Guo |
| 11,278,937 | B2 | 3/2022 | Kumar et al. |

(Continued)

FOREIGN PATENT DOCUMENTS

| | | |
|---|---|---|
| CA | 2688805 C | 7/2013 |
| CA | 3061736 A1 | 6/2019 |

(Continued)

OTHER PUBLICATIONS

Van Den Broek, W.H.A.M. et al., "Plastic material identification with spectroscopic near infrared imaging and artificial neural networks", Analytica Chimica Acta 361 (1998) 161-176.

(Continued)

*Primary Examiner* — Yoshihisa Ishizuka

(74) *Attorney, Agent, or Firm* — Oyen Wiggs Green & Mutala LLP

(57) ABSTRACT

A system and method for classifying a material in a heterogeneous mixture of materials, and predicting a processing method for treating the material are disclosed. At least some of the heterogeneous mixture of material pieces comprise different chemical information such as different chemical composition and/or physical characteristics. Embodiments of the system and method of the present invention use machine learning to classify and predict a processing protocol for material pieces based on the chemical compositions or reactivities of each of the material pieces.

20 Claims, 8 Drawing Sheets

(56)　　　　References Cited

U.S. PATENT DOCUMENTS

| | | | |
|---|---|---|---|
| 11,341,412 | B1 | 5/2022 | Fornari et al. |
| 11,427,955 | B2 | 8/2022 | Park |
| 11,475,359 | B2 | 10/2022 | Alvarez et al. |
| 2010/0205124 | A1* | 8/2010 | Ben-Hur ................. G06N 20/10 |
| | | | 706/12 |
| 2014/0379588 | A1 | 12/2014 | Gates et al. |
| 2015/0027040 | A1 | 1/2015 | Redden |
| 2017/0232479 | A1 | 8/2017 | Pietzka et al. |
| 2018/0070527 | A1 | 3/2018 | Richt |
| 2018/0075545 | A1 | 3/2018 | Richt |
| 2018/0359976 | A1 | 12/2018 | Millar et al. |
| 2020/0013024 | A1 | 1/2020 | Armstrong et al. |
| 2020/0401111 | A1* | 12/2020 | Zubarev ............. G05B 13/0265 |
| 2021/0065851 | A1* | 3/2021 | Madrid .................. G16C 20/70 |
| 2021/0224927 | A1 | 7/2021 | Perry et al. |
| 2022/0012519 | A1 | 1/2022 | Treboux et al. |
| 2022/0101276 | A1* | 3/2022 | Banatao ................. G16C 20/30 |
| 2022/0101277 | A1 | 3/2022 | Banatao et al. |
| 2022/0167606 | A1 | 6/2022 | Janssen et al. |
| 2022/0179321 | A1 | 6/2022 | Ma et al. |
| 2023/0186254 | A1 | 6/2023 | Chen et al. |
| 2024/0266005 | A1* | 8/2024 | Holiday ................ G16C 20/80 |

FOREIGN PATENT DOCUMENTS

| | | | |
|---|---|---|---|
| CA | 3105299 | A1 | 1/2020 |
| CA | 3145324 | A1 | 12/2020 |
| CN | 101493449 | B | 6/2012 |
| CN | 103709038 | B | 1/2016 |
| EP | 0612996 | A2 | 8/1994 |
| EP | 0824042 | A1 | 2/1998 |
| EP | 0494110 | B1 | 8/1999 |
| EP | 3656525 | B1 | 10/2023 |
| JP | 2009173732 | A | 8/2009 |
| JP | 6679188 | B1 | 4/2020 |
| KR | 101197724 | B1 | 11/2012 |
| WO | 2016025848 | A1 | 2/2016 |
| WO | 2021081213 | A1 | 4/2021 |
| WO | 2021216655 | A1 | 10/2021 |
| WO | 2022038052 | A1 | 2/2022 |
| WO | 2022170273 | A1 | 8/2022 |
| WO | 2022171788 | A1 | 8/2022 |

OTHER PUBLICATIONS

Zulkifley, M.A. et al., "Robust Identification of Polyethylene Terephthalate (PET) Plastics through Bayesian Decision", PLOS One, Dec. 8, 2014, https://doi.org/10.1371/journal.pone.0114518.

* cited by examiner

METHODS AND SYSTEMS FOR TREATING A HETEROGENEOUS MIXTURE OF MATERIALS

CROSS-REFERENCE TO RELATED APPLICATION

This application is a continuation of PCT application No. PCT/CA2024/050619 filed 7 May 2024, which claims priority from U.S. application No. 63/464,724 filed 8 May 2023 and entitled METHODS AND SYSTEMS FOR TREATING WASTE MATERIALS which is hereby incorporated herein by reference for all purposes. This application claims the benefit under 35 U.S.C. § 119 of U.S. application No. 63/464,724 filed 8 May 2023 and entitled METHODS AND SYSTEMS FOR TREATING WASTE MATERIALS which is hereby incorporated herein by reference for all purposes.

FIELD OF THE INVENTION

The invention pertains to methods and systems for treating materials, in particular, to predict a processing protocol for treating a heterogeneous mixture of materials, such as waste materials, with unknown or unverified chemical information.

BACKGROUND

The use of machine-learning algorithms to classify materials is known in the art. Conventional systems and methods involve sorting materials based on fixed groups or classifications, for example, by using a classification algorithm to sort unknown materials into fixed groups based on static physical or chemical information. There is a need for an improved system and method capable of classifying an unknown material beyond using only its spectral attributes and in a dynamic manner, therefrom sorting the unknown material by how it can be handled with accuracy and reliability.

SUMMARY

The invention provides systems for categorizing material pieces of unknown materials information (e.g., chemical information of the material pieces which may comprise the composition and/or physical characteristics of the pieces) and predicting a processing protocol for treating the material pieces. The material pieces may comprise a heterogeneous mixture of material pieces. The system may comprise one or more sensor systems configured to capture material information about a materials piece. The material information may be a spectrum of the material piece in response to an interaction of the material with external stimuli, for example, an electromagnetic interaction in a specified frequency range or other physical attributes. In some embodiments, the frequency range is in the infrared frequency range, but other frequency ranges may be used. The sensed information is then transmitted to a computer system to be processed by a machine-learning system. The machine-learning system is initially trained to generate a machine-learning model capable of taking inputs to produce an assessment (e.g., one or more processing methods). The initial training may comprise performing a plurality of experiments on a control set of samples. The plurality of experiments may comprise acquiring a materials information about the material by one or more sensor systems, treating the material or the mixtures of the materials using a processing protocol from a plurality of processing protocols that identifies conditions for processing materials, obtaining an output of the treatment, and analyzing the output to obtain training results. The sensed information, processing protocol, and training results may be inputted into the machine-learning system in order to train the machine-learning algorithms in the system to find correlations among the sensed information about the material piece, processing protocol, and output, thereby learning the relationship between the treatment conditions (i.e., as suggested by the output) and the different chemical reactivities or compositions, or more generally characteristics of the material pieces based on their sensed materials information (e.g., as captured by a sensor). The training operation results in a machine-learning model capable of classifying at least some of the desired materials to be treated, and/or predicting one or more processing protocols therefor.

In some embodiments, the machine-learning system is used to classify and predict one or more processing protocols for a material piece from a heterogeneous mixture of material pieces. The machine-learning system is configured to receive information about the material piece (e.g., a spectrum) and then creates, by the knowledge base or the machine-learning model, a new processing protocol for processing the material pieces based on the sensed information. The machine-learning system may be configured to connect the data containing the sensed information of the unknown material piece to the knowledge base containing the training data to infer the classification of the unknown material, and therefrom predict one or more processing protocols for treating the unknown material. The material piece is treated with the conditions identified in the predicted new processing protocol. The output of the treatment is analyzed. The sensed materials information of the unknown material, the treatment approach, and/or the output then becomes further training data for updating the machine-learning model. The process is repeated for each unknown material to be tested, resulting in an improved and more accurate, machine-learning model after each assessment.

Aspects of the invention relate to methods for categorizing material pieces of unknown materials information and predicting one or more processing protocols for treating the material pieces. The material pieces may be a heterogeneous mixture of pieces.

In some embodiments, the method comprises performing a plurality of experiments on a control set of a heterogeneous mixture of materials. Each one of the plurality of experiments may comprise acquiring a materials information about the material by one or more sensors, treating the material using a processing protocol from a plurality of processing protocols that identifies conditions for processing materials, obtaining an output of the treatment, and analyzing the output to obtain training results of the experiments. A machine-learning model may be created by training a machine-learning algorithm using the acquired materials information, the protocol, and the training results from each of the plurality of experiments. In some embodiments, the method comprises receiving an input for a desired material for treating, wherein the input comprises materials information about the desired material obtained by the one or more sensors. One or more new groupings and processing protocols for treating the desired material based on the input may be created by the machine-learning model. The desired material may be treated by using the one or more new processing protocols. An output from treating the desired material may be obtained and analyzed to obtain further training results. In some embodiments, the machine-learning model is updated by further training the machine-learning algorithm using the input, the one or more new processing protocols, and the further training results.

One non-limiting example application of the systems and methods of the present invention is in the field of waste management, and in some specific examples, waste recycling. In such examples, the material pieces comprise waste materials. In some embodiments, the systems and methods of the present invention categorize waste materials of unknown information from a heterogeneous mixture of waste materials and predict one or more processing protocols for treating the waste materials with accuracy and reliability.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Example Embodiments

Figure 1:
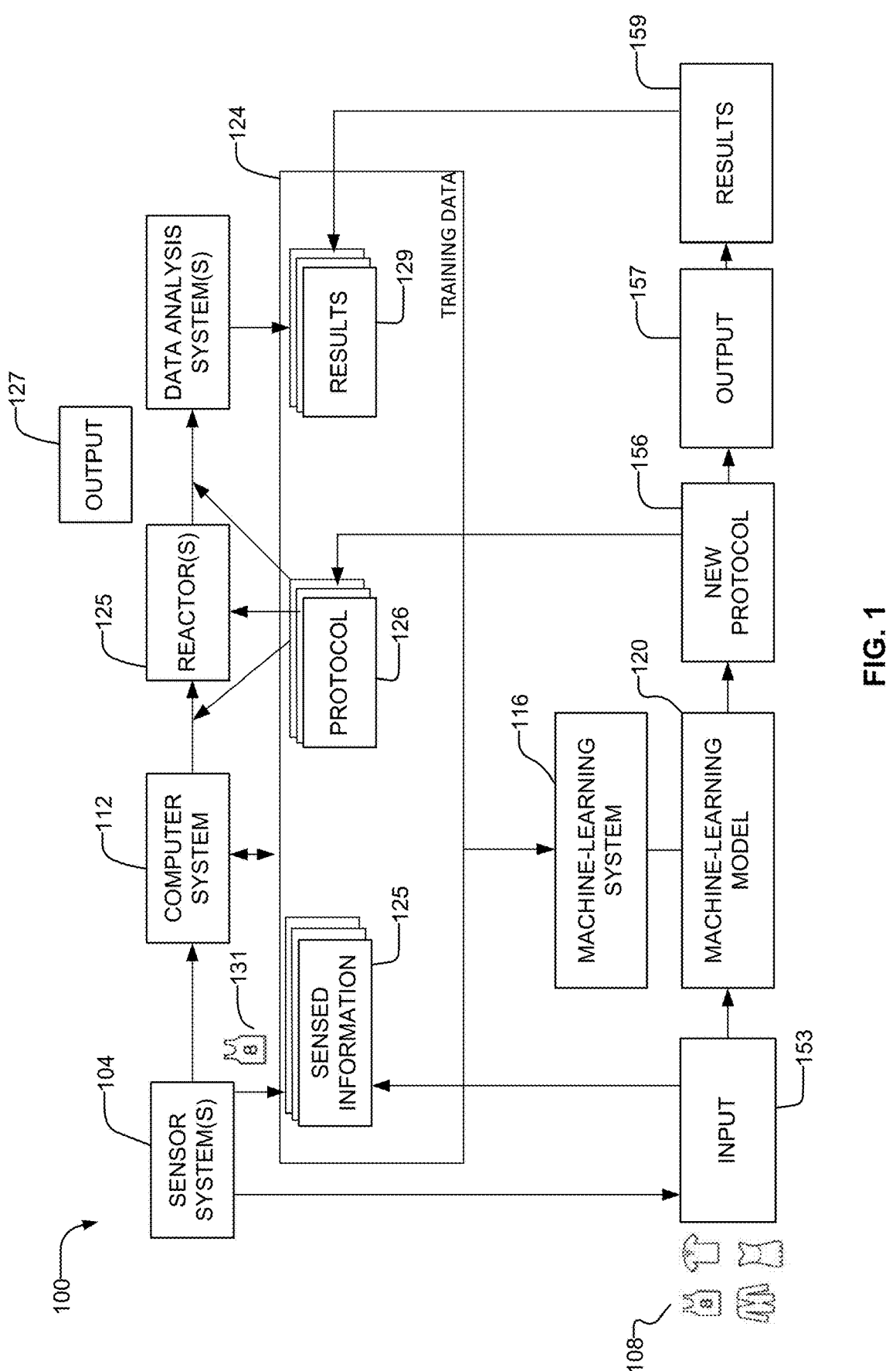
FIG. 1 is a block diagram illustrating a system for determining a recipe for treating a material piece according to an example embodiment.

Referring to FIG. 1, in one embodiment, the invention is a system 100 for categorizing material pieces of unknown materials information properties and determining a processing protocol for treating the material pieces. As used herein, a "processing protocol" includes any suitable one or more steps of a method to treat a material piece. Any one or more of chemical, thermal, biological, and physical methods may be used to treat the material piece. Non-limiting example methods that may be used to treat the material piece include titration, acidification, neutralization, saponification, precipitation, ion exchange, oxidation and reduction, polymerization, depolymerization, incineration, solidification, flotation, sedimentation, evaporation, filtration, solvation, hydrolysis, glycolysis, alcoholysis, ammonolysis, etc. The processing protocol may comprise methods of treating the material pieces inside and/or outside of the reactor. The processing protocol may include one or more processing protocols. In embodiments in which the system 100 is configured to determine more than one processing protocol, more than one processing protocol may comprise one or more processing protocols for treating the material pieces in a reactor and/or one or more processing protocols for treating the material pieces outside of the reactor. In some embodiments, the processing protocol comprises one or more processing protocols for treating the material pieces in the reactor combined with one or more processing protocols for treating the material pieces outside of the reactor. In such embodiments, the one or more processing protocols for treating the material pieces outside of the reactor may be method steps that are performed before and/or after the treating of the material pieces in the reactor.

Each of the material pieces may comprise a single material, or a composite material (i.e., a material produced from a combination of two or more materials comprising different physical and/or chemical properties). In some embodiments, the materials comprise a heterogeneous mixture of material pieces. A heterogeneous mixture of material pieces may refer to any one or more of: a mixture comprising different types of material pieces (e.g., metals versus polymers); a mixture comprising material pieces that are of the same type but belong in different classes (e.g., thermoplastics versus thermosets); a mixture comprising material pieces that are in the same class but belong in different subclasses (e.g., polyurethane versus polyethylene terephthalate); and more broadly, a mixture comprising material pieces that comprise different chemical compositions, chemical properties, and/or physical properties.

The system 100 may comprise one or more sensor systems 104 configured to capture material information about a material piece 108. The term "materials information" comprises, among other information about the materials, chemical information about the materials such as the material composition and/or the physical characteristics of the material piece. For example, the sensor system 104 may be configured to collect one or more information about a material piece 108 that can be used (e.g., in conjunction with a machine-learning system) within the system 100 to identify and/or classify the material piece 108 as a function of a set of one or more chemical and/or physical characteristics, including the chemical composition of the materials, the amount of additives such as dyes, coloring agents, catalysts, plasticizers, and coatings present in the materials, the chemical properties or the reactiveness of the materials, degree of elasticity, stiffness, strength, fineness of the materials, and/or the heterogeneity of the materials, etc.

Non-limiting examples of sensor systems 104 that may be used include sensors which use irradiated or reflected electromagnetic radiation (such as infrared ("IR"), Fourier Transform IR ("FTIR"), Forward-looking Infrared ("FLIR"), Very Near Infrared ("VNIR"), Near Infrared ("NIR"), Short Wavelength Infrared ("SWIR"), Long Wavelength Infrared ("LWIR"), Medium Wavelength Infrared ("MWIR"), X-Ray Transmission ("XRT"), Gamma Ray, Ultraviolet, X-Ray Fluorescence ("XRF"), Laser-Induced Breakdown Spectroscopy ("LIBS"), Raman Spectroscopy, Simulated Raman Spectroscopy, Anti-stokes Raman Spectroscopy, Hyper-Raman Spectroscopy, Brillouin Spectroscopy, Gamma Spectroscopy, Hyperspectral Spectroscopy, Acoustic Spectroscopy, Nuclear Magnetic Resonance (NMR) Spectroscopy, Microwave Spectroscopy, Terahertz Spectroscopy).

One or more other identification sensors may be used alone and or in combination with the sensor system 104 to assist with classifying and/or sorting of the materials pieces. In some embodiments, the other identification sensors are configured to classify material pieces as a function of one or more textures, shapes, colors, thicknesses, wettability, moisture levels, etc. Non-limiting examples of other identification sensors that may be used include, for example, optical or vision sensors, chemical sensors, radioactive sensors, hyperspectral cameras, mass sensors, force sensors, capacitance proximity sensors, etc.

In one example embodiment of the invention, the one or more sensor systems 104 comprise an infrared sensor configured to measure and/or detect the absorbance signals from a material piece at the illuminated range of wavelengths (e.g., about 700 nanometers (nm) to about 1 millimeter (mm) across the infrared region). The signals may be used to provide physical and chemical information unique to the tested material piece. Such information is used to classify each of the tested material pieces. The chemical information may for example be provided in the form of a spectrum in response to an interaction of the material with external stimuli, for example, an electromagnetic interaction in a specified frequency range. In some embodiments, the chemical information may be provided in the form of a spectrum of the material piece in a specified frequency range.

The sensed information captured from the material pieces may then be transmitted to a computer system 112, to be processed by a machine-learning system 116 in order to classify the material piece and to predict one or more processing protocols for treating the material piece. The machine-learning system 116 may implement any suitable machine-learning system, including one that implements a neural network (e.g., artificial neural network, deep neural network, convolutional neural network, recurrent neural network, autoencoders, reinforcement learning, etc.), supervised learning, unsupervised learning, semi-supervised learning, reinforcement learning, self learning, feature learning, sparse dictionary learning, anomaly detection, robot learning, association rule learning, fuzzy logic, artificial intelligence ("AI"), deep learning algorithms, deep structured learning hierarchical learning algorithms, support vector machine ("SVM") (e.g., linear SVM, nonlinear SVM, SVM regression, etc.), decision tree learning (e.g., classification and regression tree ("CART"), ensemble methods (e.g., ensemble learning, Random Forests, Bagging and Pasting, Patches and Subspaces, Boosting, Stacking, etc.), dimensionality reduction (e.g., Projection, Manifold Learning, Principal Components Analysis, Autoencoder, etc.), language models (e.g., large language models, natural language processing), and/or deep machine-learning algorithms.

In some embodiments, the machine-learning system 116 implements one or both of supervised learning, self-supervised learning, semi-supervised learning, and unsupervised learning. Supervised learning uses prior knowledge (such as experimental data that correlate inputs to outputs) to learn the relationships between the inputs and the outputs, so as to create a machine-learning model that can implement the same relationships when given inputs to generate the corresponding outputs. Examples of supervised learning algorithms include Gaussian Process (GP), Naive-Bayes, Logistic regression (LR), Random Forest (RF), neutral networks (NN), deep neural networks (DNN), matrix factorization and Support Vector Machines (SVM). Unsupervised learning may be configured to train an algorithm using information that is neither classified nor labeled, and allowing the algorithm to act on that information without guidance, by for example grouping similar points together. Examples of unsupervised learning algorithms include K-means clustering, density-based spatial clustering of applications with noise, spectral clustering, hierarchical clustering, principal component analysis, and autoencoders.

In some embodiments, the machine-learning system 116 is initially trained to generate a machine-learning model 120 that is capable of taking inputs 153 to produce an assessment (e.g., one or more processing protocols 156). In some embodiments, the machine-learning system 116 is trained by inputting into the machine-learning system 116 training data 124 comprising one or more of the sensed information about a control sample 125 (e.g., a spectrum of the material piece in a specified frequency range), processing protocol(s) 126 (e.g., processing conditions), and output 127 including results 129 of the treatment. The machine-learning algorithms in the system 116 use the training data 124 to find correlations among the sensed information about the material piece 125, processing protocol(s) 126, and results 129 of the output 127, thereby learning the relationship between the optimal treatment conditions (i.e., as suggested by the output) and the different chemical reactivities or compositions or more generally, characteristics of the material pieces based on their sensed information (e.g., as captured by an IR sensor) and processing outcomes. Some non-limiting examples of training algorithms include linear regression, gradient descent, feed forward, polynomial regression, learning curves, regularized learning models, GP, and logistic regression.

In some embodiments, in the initial training operation, the training data 124 is obtained by performing a plurality of experiments for treating a material piece. The experiments may be performed on a control sample set 131. The control sample set 131 may preferably include material pieces of different types, classes, subclasses and/or different chemical compositions. In some example embodiments, the experiments may begin with acquiring material information from each of the material pieces in the control sample set 131. In one example embodiment, the information comprises data captured by an infrared ("IR") spectroscopy, which provides information on the chemical fingerprint of the material piece. The material information may for example be a spectrum of the material piece in a specified frequency range. Each of the material pieces may be treated by one or more processing protocols 126 which identify the conditions for treating the particular material piece. The conditions for processing the material piece may be determined from statistical methods such as design of experiments or Bayesian optimization. The material piece is then treated in a reactor 125 in accordance with the conditions identified in the processing protocol. The output 127 of the treatment may be analyzed to obtain training results 129. Analysis of the output 127 of the treatment may for example comprise comparing the training results 129 to known standards (e.g., industry-specific standards) to determine the desirability of the output, and thereby the suitability of the processing protocol(s) used for the treatment. In some embodiments, the treatment processing protocol(s) may be adjusted based on the training results 129 of the output 127, and the experiment may be repeated using an improved one or more processing protocols, for example in the treatment of another material piece with similar chemical information (e.g., reactivity or composition). In some embodiments, the experiment is repeated until all of the material pieces in the control sample set 131 is tested either individually or as mixture.

In some embodiments, the number of experiments ranges from about 10 to about 5000, or in the range of from about 10 to 1500, or in the range of from about 10 to 500, or in the range of from 10 to 150 in some embodiments. The training operation may curate sufficient data to allow the machine-learning algorithms to classify at least some common material outcome of interest. In embodiments of this invention, the machine-learning algorithms continue to be trained, and the machine-learning model 120 continues to be optimized, after the initial training operation, for example during actual assessments. The starting training data 124 may comprise a limited amount of data. Embodiments of the present invention accelerate the discovery of the processing parameters of not-seen-before materials by harnessing data from previously encountered materials. These previously encountered materials may not have the same chemistry as the new materials. In doing so, the present invention bypasses the need to collect large amounts of data for every new material, which would require large amounts of empirical knowledge, computing resources, and time, before performing actual processing.

In some embodiments, other data may be used for the training operation, such as data obtained from the literature. In such embodiments, natural language processing machine learning algorithms may be used.

Referring to FIG. 1, after the machine-learning system 116 has been trained, the machine-learning system 116 is used to classify and predict one or more processing protocols for a material piece from a heterogeneous mixture of material pieces. The machine-learning system 116 is configured to receive a sensed information 153 of the material piece 108 (e.g., a spectrum of the material piece in a specified frequency range) and then creates, by the knowledge base or the machine-learning model 120, one or more new processing protocols 156 for processing the material piece based on the sensed information. The machine-learning system 116 may be configured to fit or match or connect the data containing the sensed information 153 of the unknown material piece to the knowledge base containing the training data 124 to infer the classification of the unknown material, and therefrom predict one or more new processing protocols 156 for treating the unknown material. In some example embodiments, the machine-learning system 116 is configured to generate one or more graphs fitted with one or more functions along the training data points. The input data 153 captured from the unknown material may then be matched or fitted or otherwise connected to the one or more functions to infer the classification of the material, thereby predict the one or more new processing protocols 156. In some embodiments, the material piece is treated in the reactor 125 with the conditions identified in the predicted new processing protocol 156. In some embodiments, the material piece is treated outside of the reactor with the conditions identified in the predicted one or more new processing protocols 156. In some embodiments, the material piece is treated in the reactor 125 with the conditions identified in the predicted one or more new processing protocols 156 and/or outside of the reactor with the conditions identified in the predicted one or more new processing protocols 156 before and/or after treatment in the reactor 125. The output 157 of the treatment is analyzed to obtain results 159. The sensed information of the unknown material 153, the processing protocol(s) 156, and/or the results 159 of the output 157 become further training data for inputting into the machine-learning system 116 to update the machine-learning model 120. The process is repeated for each unknown material to be tested. The accuracy and/or reliability of the machine-learning model 120 thus increases with each additional further training data.

The machine-learning system 116 of this invention may be configured to infer the classification of the unknown material, based on the knowledge base created in the machine-learning system 116 at the time of processing of the particular material. In some embodiments, the machine-learning system 116 is configured to fit the input data 153 captured from the unknown material to the knowledge base at the time of processing (e.g., in the form of one or more graphs) to infer the classification of the unknown material for predicting one or more new processing protocols 156. Since the knowledge base of the machine-learning system 116 is fluid, i.e., not fixed, and changes over time as the machine-learning system 116 is being utilized for actual assessments, the group or category within which each unknown material may be classified is also fluid. With the addition of further training data being inputted into the system 116, the knowledge base may change, and thereby the groups or categories or broadly, the correlations learned by and known to the machine-learning system 116 may also change. In embodiments of this invention, the material piece of unknown composition is dynamically mapped to a fluid (or unknown) group or category in the machine-learning system 116 to predict one or more new processing protocols 156.

In some embodiments, the output of the treatment may be supplied to one or more apparatuses or systems for downstream processing. Examples of such apparatuses and systems include purifiers, separators, reactors, etc. The output may be processed by one or more downstream processing methods to produce a final product. The final product may be analyzed to determine the desirability of the final product. Information about the final product may be inputted into the machine-learning system 116 as "additional further training data" for updating the machine-learning model 120.

In some embodiments, the material piece may be supplied to one or more apparatuses or systems for pre-treatment (i.e., before inputting the material piece into the reactor 125 for treatment). The material piece may be pre-treated by one or more pre-treatment methods to produce a pre-treated material for input into the reactor 125. In some embodiments, information about the final product comprises information on the desirability or suitability of the pre-treatment steps.

Example features that may be used for the machine-learning model 120 to predict the processing protocol 156 may comprise the sensed information of the material piece 125, 153 (e.g., signals from sensors), the processing protocol 126, 156 containing one or more processing methods and/or steps and/or reaction conditions, and results 129, 159 of the output 127, 157 and/or final product (e.g., yield (%), purity, crystal structure, crystallinity, defects, mechanical properties, size, color, durability, etc.). In some example embodiments, the reaction conditions that define the processing protocol 126, 156 comprise one or more of temperature parameters (e.g., chamber temperature, reservoir temperature, etc.), pressure parameters (e.g., chamber pressure, reservoir pressure, etc.), timing parameters (e.g., step duration, residence time, etc.), chemistry parameters (e.g., type (s) of solvent(s), concentration(s) of solvent(s), etc.), flow parameters (e.g., flow rates, etc.). In some example embodiments, the methods or steps that define the processing protocol 126, 156 comprise one or more pre-treatment and/or post-treatment methods, such as method types and/or steps. Reaction conditions including for example temperature parameters, pressure parameters, reaction geometry parameters, chemistry parameters, flow parameters, etc.

Any suitable technique to construct, optimize, and utilize a machine-learning system may be used. In an example technique, data captured by one or more sensors with respect to a particular material piece may be processed as an array of data values. For example, the data may be spectra captured by an IR camera or other sensors with respect to a particular material piece and processed as an array of values. Each data value may be represented by a single number, or as a series of numbers representing values. These values are multiplied by the weight parameters and algebraically processed to create another array of values. This process may be repeated with different weight values. Each such iteration of the process is known as a "layer" of the neural network. Each layer may serve a specific function such as feature engineering, feature extraction, data smoothing, and dimensionality reduction. The outputs of the final layer may be interpreted as probabilities that a particular chemical characteristic is present or absent in the captured data pertaining to the material piece.

In accordance with embodiments of the present disclosure, the final set of outputs is trained to represent the likelihood that a chemical attribute is present based on the captured data. These techniques can be extended to determine not only the similarity between materials based on the captured data, but also to connect with additional machine-learning algorithms to predict the processing protocol and reactivity of material based on the reaction outcomes of previously encountered materials. This additional connection may be based on classification methods such as LR, decision tree, RF, Naive-Bayes, SVM, or regression methods, such as GP, random forest, logistic regression, gradient boost, neutral net, or based on another set of neural networks. This allows for a grouping decision and processing parameters to be determined.

Figure 2:
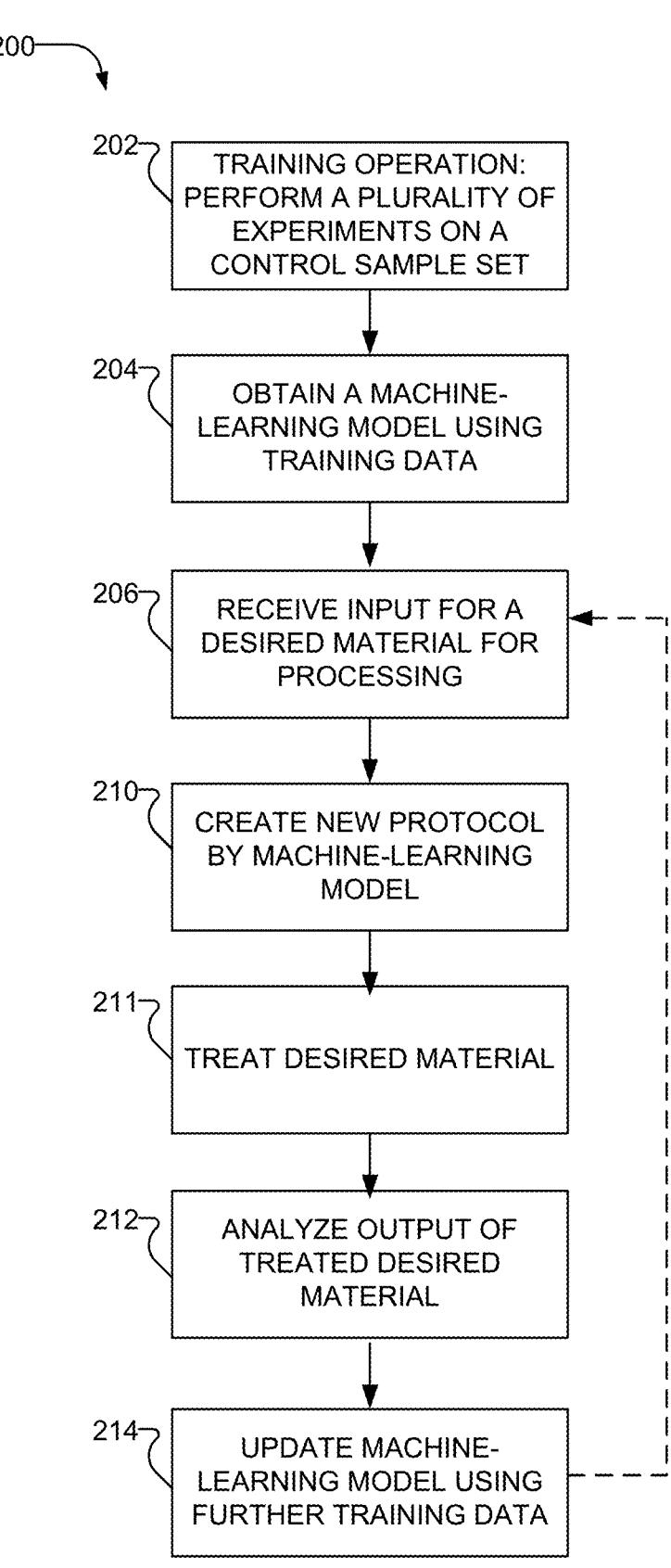
FIG. 2 is a block diagram illustrating example features used by the machine-learning system according to an example embodiments.

An aspect of the invention relates to a method for classifying materials of unknown materials information, and determining a processing protocol for treating the materials. FIG. 2 is a flow chart illustrating an example method 200 according to an embodiment of the invention. The method comprises performing a plurality of experiments for treating a material piece (step 202). The plurality of experiments may be performed on a control sample set comprising a mixture of heterogeneous material pieces. Each experiment is controlled by one or more processing protocol(s) from a plurality of processing protocols that identify conditions for treating the material piece. The experiment may comprise acquiring the information of the material by one or more sensors, treating the material using the processing protocol (s), obtaining an output of the treatment, and analyzing the output to obtain experimental results. At step 204, a machine-learning model or knowledge base is obtained by training a machine-learning algorithm using the experimental results, comprising one or more of the sensed information from the material piece (e.g., a spectrum), processing protocol(s) (e.g., processing protocols and conditions), and output (e.g., results of the treatment). Once the machine-learning model has curated sufficient data, the method 200 flows to step 206 for receiving input (e.g., a spectrum) from a desired material piece of unknown information for treatment of the material piece. At step 210, the machine-learning model creates one or more new processing protocols for treating the material piece based on the input. The material piece may be treated based on the new processing protocol(s) (step 211). The output of the treatment may then be analyzed (step 212). At step 214, the machine-learning model or knowledge base is updated after treatment of each material piece, for example, the sensed information from the material piece, new processing protocol(s), and output may be inputted to the machine-learning algorithm for continuous training or finding new correlations after each treatment.

An aspect of the invention relates to a system that includes a memory comprising instructions and one or more computer processors. The instructions, when executed by the one or more computer processors, cause the one or more computer processors to perform operations comprising: performing a plurality of experiments for treating a material piece, each experiment being controlled by a processing directive from a plurality of processing protocols that identifies conditions for treating material pieces; generating a machine-learning model by training an machine-learning algorithm using experiment results comprising one or more of the sensed information from the material piece (e.g., the absorbance signals on a IR spectrum), processing protocol (e.g., reaction conditions for processing), and output (e.g., results of the treatment); receiving input for treating a desired material piece; creating, by the machine-learning model, a new processing protocol for treating the material piece based on the input; and updating the machine-learning model by inputting the sensed information from the material piece, new processing protocol, and output.

An aspect of the invention relates to a machine-readable storage medium (e.g, a non-transitory storage medium) includes instructions that, when executed by a machine, cause the machine to perform operations comprising: performing a plurality of experiments for treating a material piece, each experiment being controlled by a processing directive from a plurality of processing protocols that identifies conditions for treating material pieces; generating a machine-learning model by training an machine-learning algorithm using experiment results comprising one or more of the sensed information from the material piece (e.g., the absorbance signals on a IR spectrum), treatment processing protocol (e.g., reaction conditions), and output (e.g., results of the treatment); receiving input for treating a desired material piece; creating, by the machine-learning model, a new processing protocol for treating the material piece based on the input; and updating the machine-learning model by inputting the sensed information from the material piece, new treatment processing protocol, and output.

Figure 3:
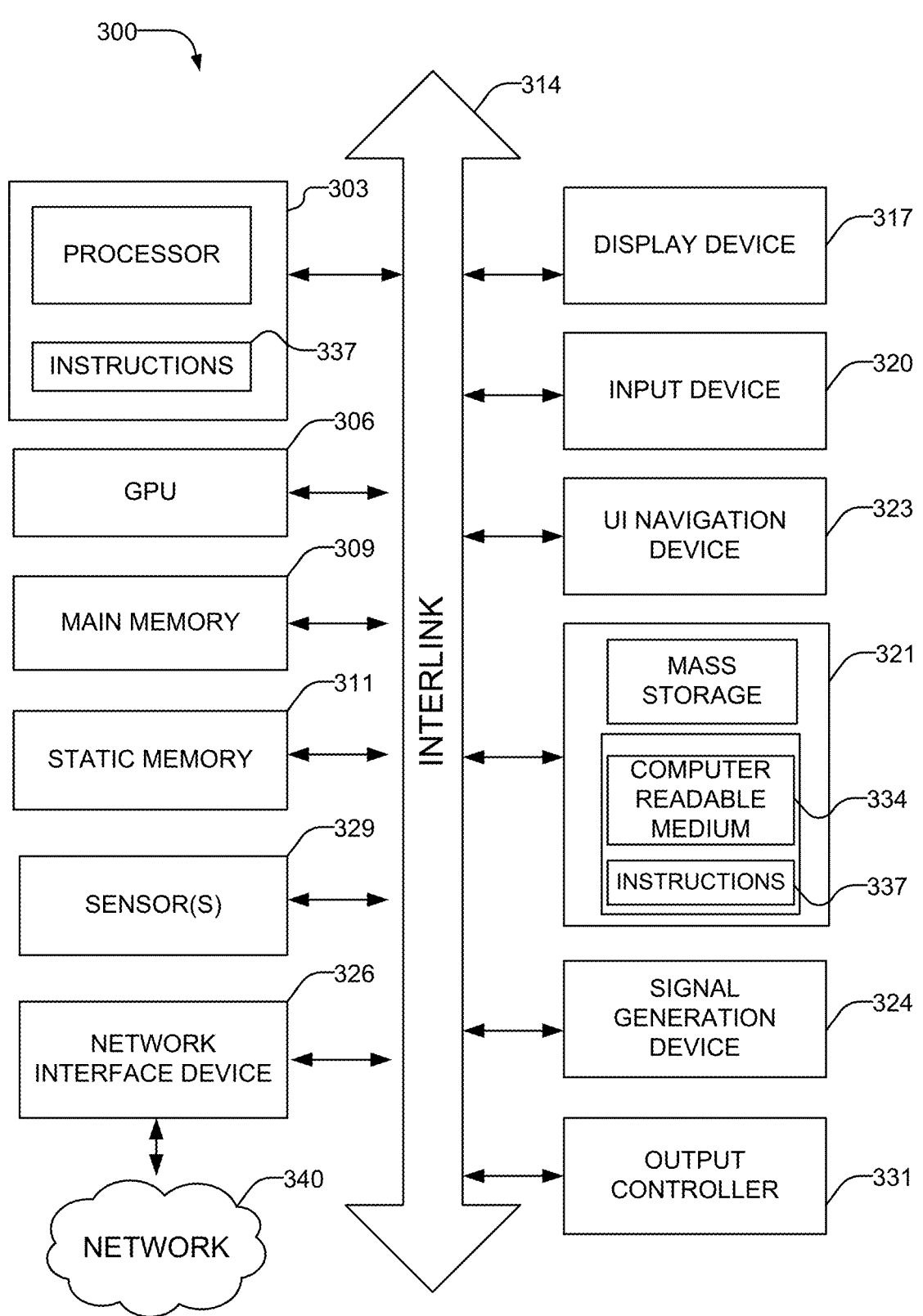
FIG. 3 is a block diagram illustrating an example computing system upon or by which one or more example embodiments may be implemented or controlled.

FIG. 3 is a block diagram illustrating an example computing system 300 upon or by which one or more embodiments described herein may be implemented. The computing system 300 may operate as a standalone device or may be connected (e.g., networked) to other computing systems.

Examples, as described herein, may include or may operate by, logic, a number of components, or mechanisms. Circuitry is a collection of circuits implemented in tangible entities that include hardware (e.g., simple circuits, gates, logic). Circuitries include members that may, alone or in combination, perform specified operations when operating. In an example, hardware of the circuitry may be immutably designed to carry out a specific operation (e.g., hardwired). For example, the hardware of the circuitry may include variably connected physical components (e.g., execution units, transistors, simple circuits) including a computer-readable medium physically modified (e.g., magnetically, electrically, by moveable placement of invariant massed particles) to encode instructions of the specific operation. In connecting the physical components, the underlying electrical properties of a hardware constituent are changed (for example, from an insulator to a conductor or vice versa). The instructions enable embedded hardware (e.g., the execution units or a loading mechanism) to create members of the circuitry in hardware through the variable connections to carry out portions of the specific operation when in operation. Accordingly, the computer-readable medium is communicatively coupled to the other components of the circuitry when the device is operating. For example, any of the physical components may be used in more than one member of more than one circuitry.

The computing system 300 may include a hardware processor 303 (e.g., one or more of a central processing unit (CPU) and a hardware processor core), a graphics processing unit (GPU) 306, a main memory 309, and/or a static memory 311, some or all of which may communicate with each other by an interlink (e.g., bus) 314. The computing system 300 may further include one or more of a display device 317, an alphanumeric input device 320 (e.g., a keyboard), and a user interface (UI) navigation device 323 (e.g., a mouse). The computing system 300 may comprise one or more of a mass storage device (e.g., drive unit) 321, a signal generation device 324 (such as a speaker), a network interface device 326, and one or more sensors 329, such as a Global Positioning System (GPS) sensor, compass, accelerometer, etc. The computing system 300 may also comprise an output controller 331, such as a connection to communicate with or control one or more peripheral devices (e.g., a printer, card reader).

The mass storage device 321 may comprise a machine-readable medium 334 on which is stored one or more sets of data structures or instructions 337 (e.g., software) embodying or utilized by any one or more of the techniques or functions described herein. The instructions 337 may be stored, completely or at least partially, within one or more of the main memory 309, static memory 344, hardware processor 303, and GPU 306 during execution thereof by the computing system 300.

The "machine-readable medium" may include a single medium, or multiple media, (e.g., a centralized or distributed database, and/or associated caches and servers) configured to store the one or more instructions 337. The "machine-readable medium" may include any medium that is capable of storing, encoding, or carrying instructions 337 for execution by the computing system 300 and which causes the computing system 300 to perform any one or more of the techniques described herein, or that is capable of storing, encoding, or carrying data structures used by or associated with such instructions 300. Non-limiting examples of machine-readable medium include solid-state memories and optical and magnetic media.

The instructions 337 may be transmitted or received over a communication network 340 using a transmission medium through the network interface device 326.

Example Application of Embodiments

One non-limiting example application of the system and method of the present invention is in the field of recycling. The waste materials may comprise one or more of plastics, textiles, paper, glass, metal, aluminum, etc. The waste material may comprise a heterogeneous mixture of one type of materials for recycling (e.g., different types of plastics such as polyethylene, polypropylene, polyethylene terephthalate, polypropylene terephthalate, polybutylene terephthalate, polyurethanes, polystyrene, polyamide, polyvinyl chloride, etc., and combinations thereof), or a heterogeneous mixture of a plurality of types of materials for recycling (e.g., different types of plastics such as polyethylene, polypropylene, polyethylene terephthalate, polypropylene terephthalate, polybutylene terephthalate, polyvinyl chloride, etc., and combinations thereof, and textiles such as linen, polyester, cotton, silk, wool, elastane, nylon, viscose, lyocell, modal, etc., and combinations thereof).

The system and method of the present invention implements machine-learning to classify a waste material of unknown composition and predict a processing protocol for chemically treating the waste material so as to recycle the waste material. The waste material may be chemically treated by depolymerization. "Depolymerization" refers to a process of chemically converting polymers (macromolecules) into monomer or oligomer components (smaller molecules that can be processed into new polymers). The monomer and oligomer components may be recycled for use to form new polymers.

The outcome of a depolymerization process (as indicated by for example the quality of the product such as purity, selectivity, and/or quantity of the product such as product yield) depends on the operating reaction conditions. The inventors recognize that the use of one single reaction condition to depolymerize materials with different chemical reactivity or compositions results in uncontrolled depolymerization outcomes. The inventors also recognize that materials of the same type, class and/or subclass, and which are collected from the same batch and with the same color can possess different chemical reactivities or compositions. The inventors have shown that desirable depolymerization outcomes can be achieved if the reaction condition and processing protocols are customized to each material and one possible way to differentiate the chemical reactivities or compositions to enable this customization is through spectroscopy. In one example embodiment, the spectroscopy comprises infrared (IR) spectroscopy.

Figure 4A:
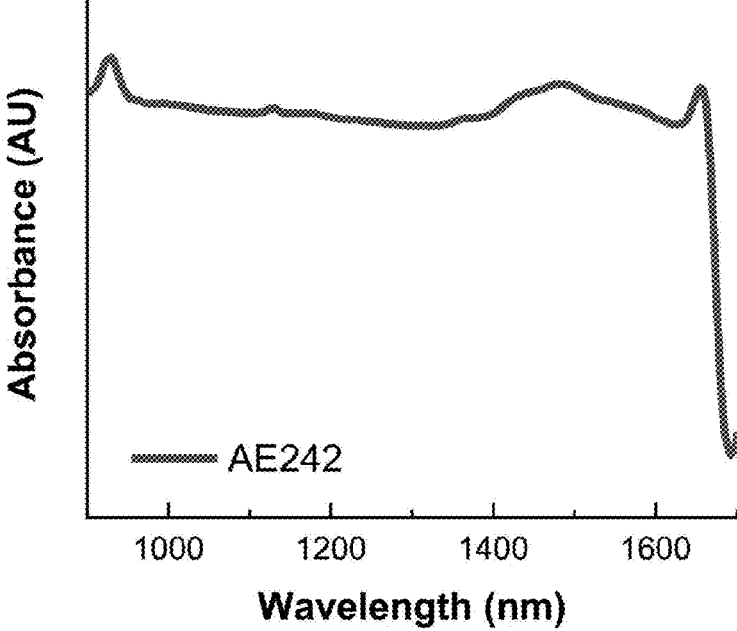
FIG. 4A shows near-infrared spectra of two polyester blend materials of the same color and product from the same brand, identified as AE00242 and AE00244.
Figure 4A:
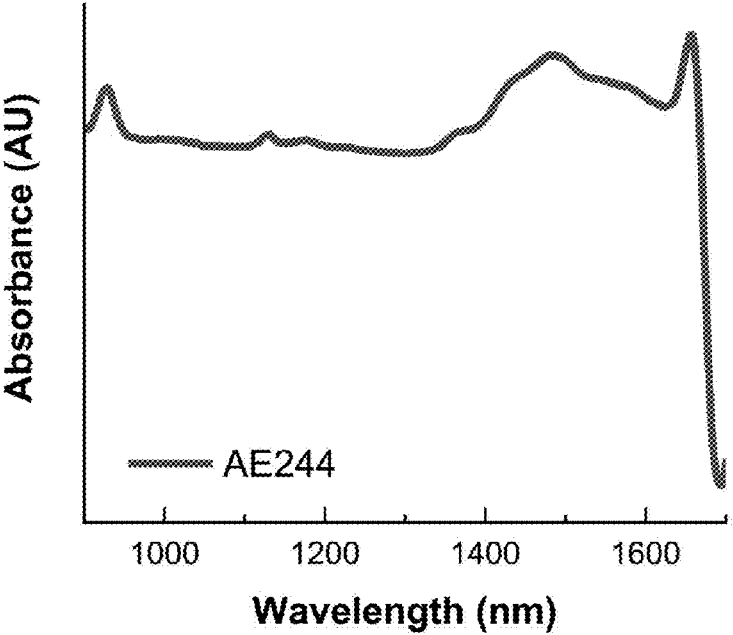

FIG. 4A illustrates near-IR spectra of two polyester blend materials identified as AE00242 and AE00244, which comprise the same color (red) and are collected from the same batch of materials. FIG. 4A spectra show that the two materials which are of the same type, color, and batch, AE00242 and AE00244, absorb and reflect at different wavelengths and thus possess different absorbance spectra.

Figure 4B:
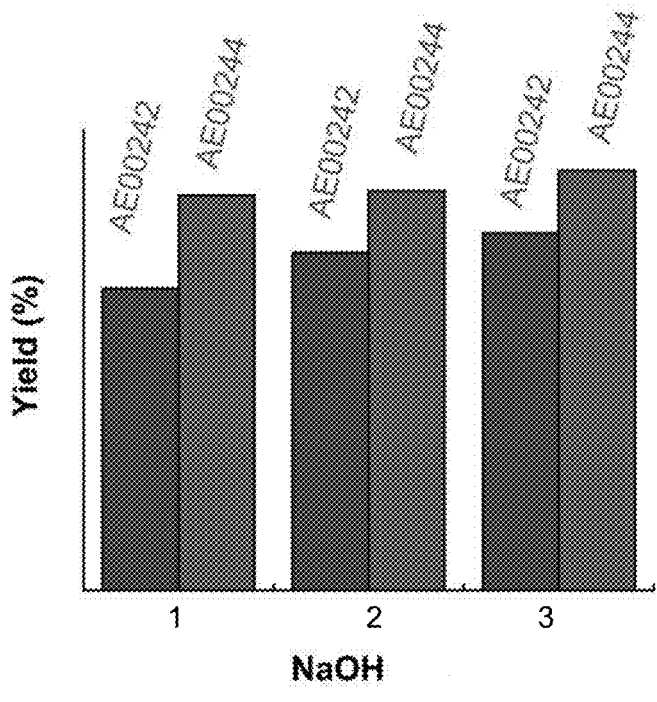
FIG. 4B is a plot showing the differences in the yield of monomer extraction (%) as treated by three different concentrations of sodium hydroxide after depolymerization using Recipe 1 and Recipe 2, of the two polyester blend materials identified as AE00242 and AE00244.
Figure 4C:
FIG. 4C is a plot showing the differences in the quality of extracted monomer (acid number) after depolymerization using Recipe 1 and Recipe 2, of the two polyester blend materials identified as AE00242 and AE00244.

FIG. 4B is a plot showing the percent (%) yield of monomer extraction from using three different concentrations of sodium hydroxide upon depolymerization of two polyester blend materials, AE00242 and AE00244, using two different recipes, denoted as Recipe 1 and Recipe 2. FIG. 4C is a plot showing the total acid number in the extracted monomers upon depolymerization of two polyester blend materials, AE00242 and AE00244, using Recipe 1 and Recipe 2. As used in this experiment, the acid number is a measure of the number of the end groups of terephthalic acid (TA) in a chemical compound by a pH indicator.

The FIGS. 4B and 4C plots illustrate that the same treatment processing protocol used in the depolymerization of material pieces with different chemical reactivities or compositions results in different depolymerization outcomes, as demonstrated by the differences in the quality and quantity of the monomers that resulted from the process.

Figure 5:
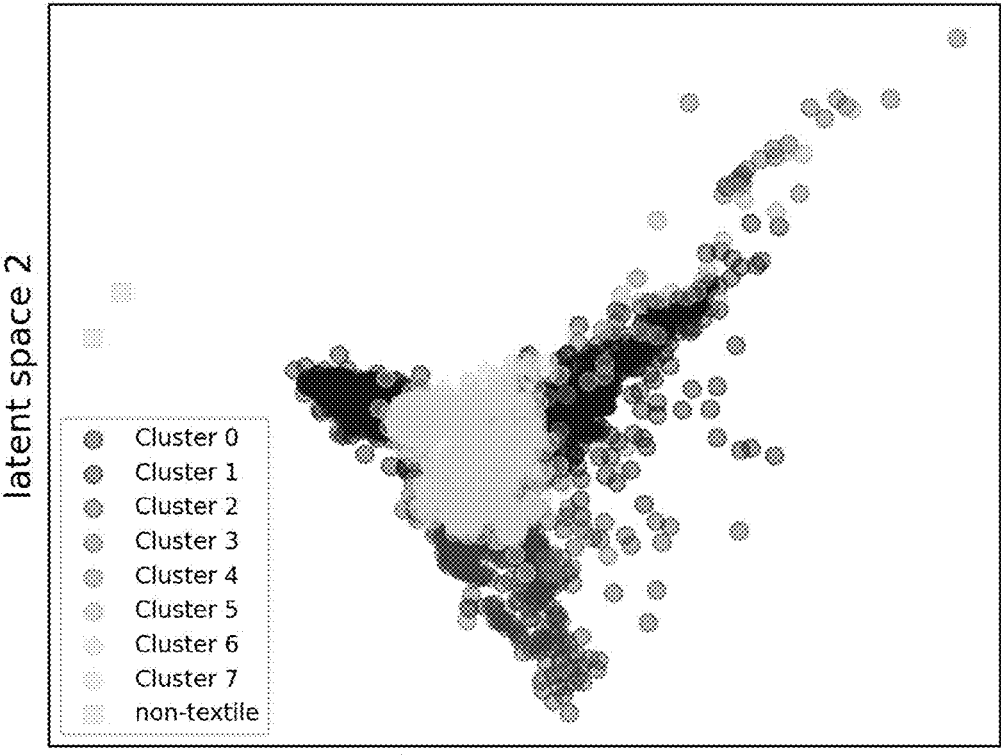
FIG. 5 is a 2D principal component plot for different groups of polyester-blend materials according to an example experiment.
Figure 6:
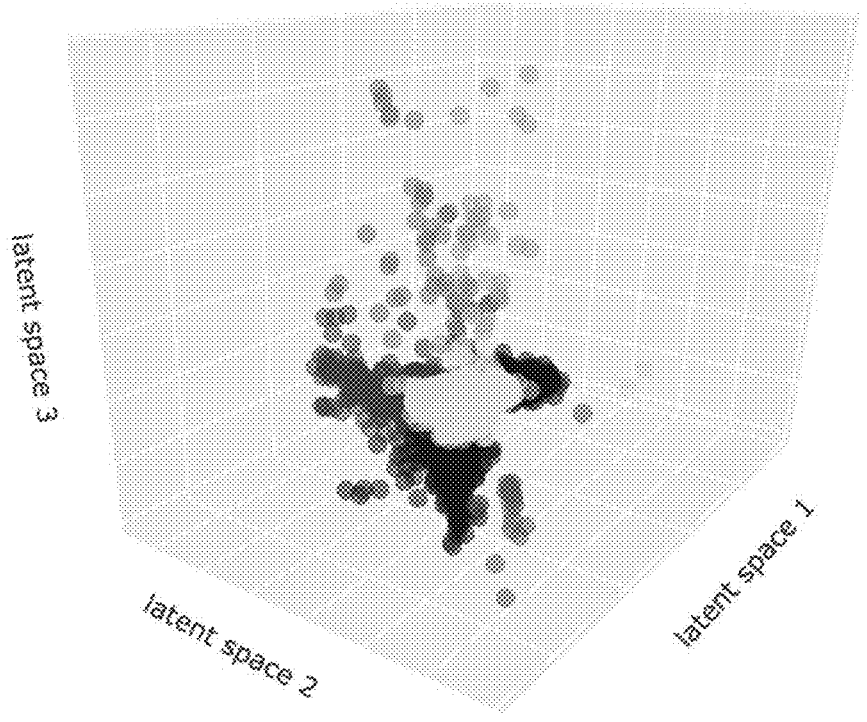
FIG. 6 is a 3D principal component plot showing the different groups of polyester-blend materials in clusters classified using machine-learning algorithms.
Figure 7:
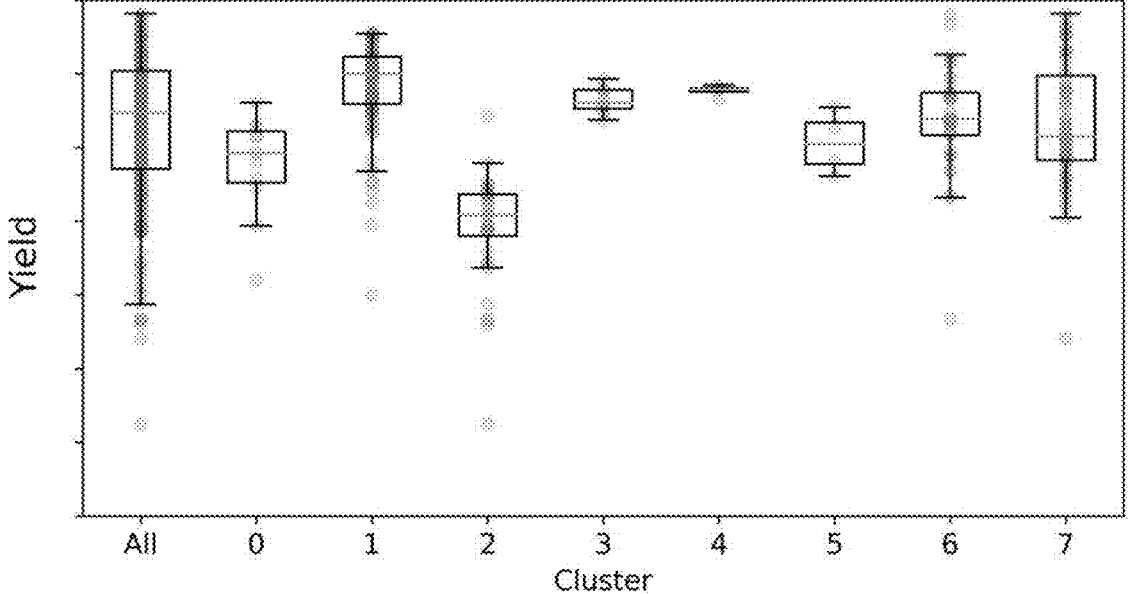
FIG. 7 shows the distribution of monomer recovery from the depolymerization of polyester-blend materials. The left-most distribution represents the distribution of depolymerization outcome for all samples (unsorted). The right distributions show the distributions of depolymerization outcome for the polyester blend classified into clusters using machine-learning algorithms.

In some example experiments, the system 100 and method 200 as described and shown in FIGS. 1 and 2 were used to predict depolymerization processing protocols for waste textile materials. One of the waste textile materials tested was polyester blends. The waste textile materials comprise a heterogeneous mixture of polyester materials, at least some of which comprise different chemical reactivities or compositions. FIG. 5 is an example 2D principal component score plot for different groups of polyester blend materials and other plastic products, plotted based on its chemical information as indicated by the spectrum obtained in response to an electromagnetic interaction of the textile materials in the infrared frequency range but labeled based on the machine-learning algorithms. FIG. 6 is a 3D principal component score plot showing the different groups of polyester blend materials and other plastic products in clusters classified using machine-learning algorithms. FIG. 7 is a plot showing the distribution of monomer recovery from the depolymerization of post-consumer polyester blend samples. The leftmost distribution represents the distribution of depolymerization outcome for all samples (unsorted). The right distributions show the distributions of depolymerization outcome for the polyester blend classified into clusters using machine-learning algorithms in FIG. 6.

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:

1. A system for predicting a processing protocol for treating a heterogeneous mixture of materials, comprising:

one or more sensor systems configured to analyze a material;

one or more processors configured to process the material;

one or more data analysis systems configured to receive and analyze an output of the material upon processing of the material;

a computer system operatively connected to the one or more sensor systems, the one or more data analysis systems, and the one or more processors, the computer system configured to perform the steps of:

receiving, from the one or more sensor systems, a materials information about a material from a control set of materials;

receiving, from the one or more data analysis systems, a training results from analysis of the output, wherein the output is produced by treating the material in the one or more processors using a processing protocol from a plurality of processing protocols that identify conditions for processing materials;

creating a machine-learning model by training a machine-learning algorithm using the materials information, the processing protocol, and the training results from each of a plurality of experiments;

receiving, from the one or more sensor systems, an input for a desired material for treating, wherein the input comprises one or more physical characteristics, a composition, or a spectral data of the desired material;

creating, by the machine-learning model, a new processing protocol and grouping strategy for treating the desired material based on the input;

communicating the new processing protocol to the one or more processors to control conditions for treating the desired material, wherein the one or more processors are configured to treat the desired material with the new processing protocol;

receiving, from the one or more data analysis systems, further training results from analysis of the output, wherein the output is produced by treating the desired material in the one or more processors using the new processing protocol; and updating the machine-learning model by further training the machine-learning algorithm by inputting the input, the new processing protocol, and the further training results.

2. The system according to claim 1 wherein the one or more sensor systems comprises an infrared sensor.

3. The system according to claim 1, wherein the one or more processors comprise one or more reactors, and wherein the one or more reactors is configured to depolymerize the material.

4. The system according to claim 3, wherein the one or more reactors is configured to alter the chemical characteristics of the material.

5. The system according to claim 1, wherein the one or more data analysis systems configured to receive and analyze the output of the material upon processing of the material comprises one or more of a monomer extraction unit configured to determine monomer extraction efficiency and an analysis unit configured to chemically or spectroscopically determine the purity and characteristics of the monomers in the output.

6. The system according to claim 1, wherein the materials information comprises a spectrum of the material in response to an electromagnetic interaction of the material in a specified frequency range.

7. The system according to claim 1, wherein the materials information comprises a composition of the material.

8. The system according to claim 1, wherein the materials information comprises one or more physical characteristics of the material.

9. The system according to claim 1, further comprising one or more apparatuses arranged upstream of the one or more processors, the one or more apparatuses being configured to pre-treat the material before inputting the material into the one or more processors.

10. The system according to claim 1, wherein the features that define the processing protocol comprises conditions for depolymerizing the material in the one or more processors to obtain a depolymerized material.

11. A system for predicting a processing protocol for treating a heterogeneous mixture of materials, comprising:

one or more sensor systems configured to analyze a material;

one or more processors configured to process the material;

one or more data analysis systems configured to receive and analyze an output of the material upon processing of the material;

a computer system operatively connected to the one or more sensor systems, the one or more data analysis systems, and the one or more reactors, the computer system configured to perform the steps of:

receiving, from the one or more sensor systems, an input for a desired material for treating;

creating, by a machine-learning model, a new processing protocol and grouping strategy for treating the desired material based on the input, wherein the machine-learning model is created by training a machine-learning algorithm using a materials information, a processing protocol, and training results obtained from analyzing an output of a treatment from a plurality of experiments performed on a control set of materials;

communicating the new processing protocol to the one or more processors to control conditions for treating the desired material, wherein the one or more processors treat the desired material with the new processing protocol;

receiving, from the one or more data analysis systems, further training results from analysis of the output, wherein the output is produced by treating the material in the one or more processors using a processing protocol from a plurality of processing protocols that identify conditions for processing materials; and updating the machine-learning model by further training the machine-learning algorithm by inputting the input, the new processing protocol, and the further training results.

12. The system according to claim 11 wherein the one or more sensor systems comprises an infrared sensor.

13. The system according to claim 11, wherein the one or more processors comprise one or more reactors and wherein the one or more reactors is configured to depolymerize the material.

14. The system according to claim 13, wherein the one or more reactors are configured to alter the chemical characteristics of the material.

15. The system according to claim 11, wherein the one or more data analysis systems comprises one or more of a monomer extraction unit configured to determine monomer extraction efficiency and an analysis unit configured to chemically or spectroscopically determine the purity and characteristics of the monomers in the output.

16. The system according to claim 11, wherein the materials information comprises a spectrum of the material in response to an electromagnetic interaction of the material in a specified frequency range.

17. The system according to claim 11, wherein the materials information comprises a composition of the material.

18. The system according to claim 11, wherein the materials information comprises one or more physical characteristics of the material.

19. The system according to claim 11, further comprising one or more apparatuses arranged upstream of the one or more processors, the one or more apparatuses being configured to pre-treat the material before inputting the material into the one or more processors.

20. The system according to claim 11, wherein the features that define the processing protocol comprises conditions for depolymerizing the material in the one or more processors to obtain a depolymerized material.

* * * * *